(12) United States Patent
Grossinger et al.

(10) Patent No.: US 7,463,356 B2
(45) Date of Patent: Dec. 9, 2008

(54) METHOD FOR ANALYZING HAIR

(75) Inventors: Nadav Grossinger, Rechovot (IL);
Israel Grossinger, Rechovot (IL); Eli Benny, Rishon-LeZion (IL); Michel Mercier, Tel-Aviv (IL); Avigdor Scherz, Rechovot (IL)

(73) Assignee: SeeThrough Ltd., Nes Ziona (IL)

( * ) Notice: Subject to any disclaimer, the term of this patent is extended or adjusted under 35 U.S.C. 154(b) by 179 days.

(21) Appl. No.: 11/328,337

(22) Filed: Jan. 10, 2006

(65) Prior Publication Data
US 2007/0159290 A1 Jul. 12, 2007

(51) Int. Cl.
G01J 3/46 (2006.01)
(52) U.S. Cl. ...................................... 356/402
(58) Field of Classification Search .................. 356/402
See application file for complete search history.

(56) References Cited

U.S. PATENT DOCUMENTS

| | | |
|---|---|---|
| 4,434,467 A | 2/1984 | Scott |
| 6,067,504 A | 5/2000 | MacFarlane et al. |
| 6,157,445 A | 12/2000 | MacFarlane et al. |
| 6,308,088 B1 | 10/2001 | MacFarlane et al. |
| 6,314,372 B1 | 11/2001 | MacFarlane et al. |
| 6,330,341 B1 | 12/2001 | MacFarlane et al. |
| 6,707,929 B2 | 3/2004 | Marapane et al. |
| 2004/0000015 A1* | 1/2004 | Grossinger et al. ............. 8/405 |
| 2005/0036677 A1 | 2/2005 | Ladjevardi |

* cited by examiner

*Primary Examiner*—Kara E Geisel

(57) ABSTRACT

An apparatus for analyzing a sample hair mixture having a mixture of two hair colors and an overall spectrum representative of the two colors, comprising: a first color selector, configured to select a first spectrum representative of a first color in the hair mixture from a first group of at least one spectrum, and an iterative spectrum combiner, associated with the first color selector and configured to iteratively combine therewith a second spectrum representative of a second color in the hair mixture from a second group of spectra over the first spectrum, thereby to find an optimal combination of first and second spectrum which is a closest match to the overall spectrum.

47 Claims, 12 Drawing Sheets
(3 of 12 Drawing Sheet(s) Filed in Color)

Fig. 10
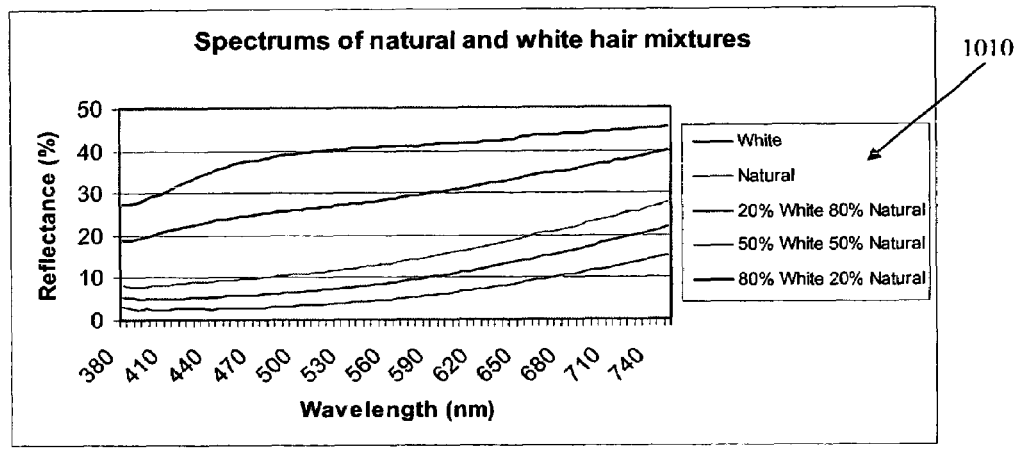
Fig.. 11
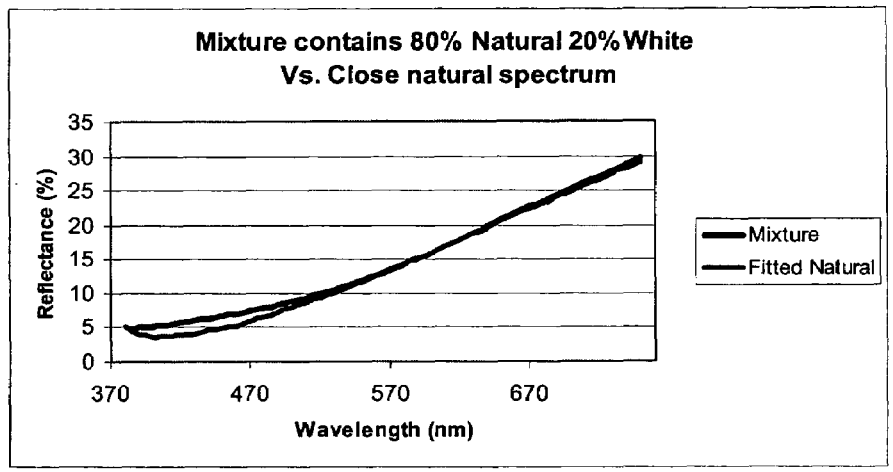
Mixture contains 80% natural hair and 20% white hair Vs. close natural spectrum fitted from database

1210

Algorithm results for extracting concentrations
of white and natural components in different mixtures.

Algorithm results for extracting natural spectrum
for mixture that appears above Example of slope spectrums difference for mixture that appears above
(80% Natural 20% white)

METHOD FOR ANALYZING HAIR

FIELD AND BACKGROUND OF THE INVENTION

The present invention relates to hair analysis and, more particularly, but not exclusively to a method and an apparatus for analyzing hair mixtures and predicting a final color when hair dyeing.

Hair dyes and bleach are used to make gray hairs less conspicuous or to dye hair a desired color. Hair dyes include temporary dyes (color shampoo, color conditioner, color treatment conditioner, etc.) that are easy to apply, the color remaining for a short time, semi-permanent dyes (hair manicure, clear-type hair manicure, etc.) that provide a dye effect that can be continuously maintained through penetration of an acidic dye into the interior of the hair, and permanent dyes that achieve an essentially permanent dye effect through oxidative polymerization of the dye in the interior of the hair. A particular type of hair dye is selected depending on the intended use.

Each of these types of dyes is prepared in numerous color numbers. Usually, each dye color is indicated on the box containing the dye, or by means of sample tresses of dyed hair.

However, even where the same color dye is used, the color of the hair after dyeing differs considerably depending on the color mixture of the hair before dyeing.

In case that the hair before dyeing has a non homogenous mixture of white hair and colored hair, the result, of current methods fail to accurately predict the hair color after dyeing. Colored hair can be natural pigmented hair or dyed with artificial colors.

Consequently, it is difficult to predict the color that will result from dyeing any person's hair solely from the printing on the box or the sample tresses, and the problem arises that the actual color of the hair after dyeing is different from the color anticipated.

There are methods to predict the final hair color in order to minimize error and increase customer satisfaction with the use of hair color products.

Some methods use a color chart or an indexed table which predicts the hair's final color after choosing the initial color from the table and the color to use. For example, U.S. patent application Ser. No. 4,434,467, entitled "Hair coloring calculator" to Scott, filed on Mar. 30, 1981 describes a device for determining the hair coloring products to be used to change the user's present hair color to a new hair color. The device includes a keyboard for entering a designation which identifies the user's present hair color and the desired hair color. The user also enters data to identify the particular line of hair coloring products which the user desires to use. The device then responds to such data by displaying the designations of hair coloring products of the chosen line which will presumably change the user's present hair color to the new hair color.

However, the Scott method and similar methods are restricted to a limited number of possibilities of initial hair colors and therefore fail to predict the exact final color to all variants of initial hairs. Furthermore, the lack of some kind of direct measurement of the customer's initial hair leaves the initial color estimation for the human eye, and prevents the methods from accurately predicting the resulting color.

U.S. patent application Ser. No. 10/473,627, entitled "Hair color measurement and treatment", to Grossinger et al, filed on Oct. 1, 2003, introduces a way to predict the spectrum of the hair reached after a dyeing process based on the initial spectrum of the hair. An underlying assumption is that the initial hair color is homogenous.

A problem emerges in that when measuring reflectances both the regular natural hair and the white hair are measured together. Thus, the reflectance spectrum received from the measurement device is a combination of both the regular and white hair. The combined spectrum is thus merely a combination of the two hair types in the measured hair and therefore may cause inaccurate final color prediction.

Other known methods perform a measurement of the initial hair color using a colorimeter of some kind (RGB or L, a, b color values which are standard methods to define color). These other methods may also be used to predict the hair color using mathematical equations that are constructed based on a database of colored hairs (U.S. Pat. No. 6,707,929) or on a color table built on a database of the same kind (U.S. Pat. Nos. 6,067,504, 6,157,445, 6,308,088, 6,314,372 and 6,330,341 to MacFarlane, et el).

However the above methods restrict themselves to the color coordinates which are not very representative of the spectrum and thus they lose accuracy and the ability to indicate on the chemical composition of the hair. For example, US Patent Publication No. 2005/0036677, entitled "Advanced cosmetic color analysis system and methods therefore" to Ladjevardi, filed on Feb. 17, 2005 describes a way to analyze the different colors in a measurement of an area of hair.

The measurement as described by Ladjevardi is taken using a digital camera which produces results in the form of a matrix of RGB values. The analysis is performed by iterating through the RGB matrix and sorting its values into some predetermined groups.

The output of the Ladjevardi method may be the concentration of each color group in the measured area. The predetermined groups are verified by a representative RGB value for each one. Presumably, since one can predetermine one group to represent white hair color, this method may be used to analyze the white hair concentration in a given hair sample.

However, since Ladjevardi's method uses RGB values as input it is limited by the resolution of the RGB. As a result of the resolution limit, each pixel in the picture generated by the camera, providing the RGB values, actually consists of a mixture of colors. The underlying mixed pure hair color spectrums are never taken into consideration.

The resolution of the RGB cannot accurately predict the final color of the hair since different spectrums which result from different pigment concentrations can produce the same RGB or L, a, b values but will react differently when treated with bleaching or dyeing agents.

Furthermore, it is known that two different hair samples with different spectrums and pigment structure may have the same color L, a, b coordinates but react differently to bleaching and color treatments.

For example, two samples of hair, which look substantially the same to the human eye may have the same L, a, b color coordinate values even though they have different spectrums of reflectance, and therefore, different concentrations of components (eumelanin pigments, Pheomelanin pigments, artificial hair color, etc).

For example, one natural blond hair sample which is colored with dye A, may have the same color coordinates as another hair sample, say, a brown hair colored with a dye B.

Moreover, a large number of hair samples, each having different reflectance spectra, may all generate the same L, a, b color coordinate values or very similar color L, a, b coordinate values. That is to say, the hair samples having different combinations of Eumelanin, Pheomelanin and keratin concentrations that result in different curves of spectrums, may produce similar color coordinate values.

However, the same hair treatment applied to these hair samples generates different final hair colors due to the different initial concentrations of each of the above materials in each of the hair samples.

As described hereinabove, currently used methods, as discussed above, fail to deal with the subject of predicting the final color of hair that contains two or more hair types with different colors. Ladjevardi deals with this problem but can only produce RGB values of each hair type, thus cannot be use with advanced color prediction methods that uses the full spectral information as input.

There is thus a widely recognized need for, and it would be highly advantageous to have, an apparatus and method devoid of the above limitations.

SUMMARY OF THE INVENTION

According to one aspect of the present invention there is provided an apparatus for analyzing a sample hair mixture having a mixture of two hair colors and an overall spectrum representative of the two colors. The message comprises: a first color selector, configured to select a first spectrum representative of a first color in the hair mixture from a first group of at least one spectrum, and an iterative spectrum combiner, associated with the first color selector and configured to iteratively combine therewith a second spectrum representative of a second color in the hair mixture from a second group of spectra over the first spectrum, thereby to find an optimal combination of first and second spectrum which is a closest match to the overall spectrum.

According to a second aspect of the present invention there is provided an apparatus for analyzing a sample hair mixture having a mixture of two hair colors and an overall spectrum representative of the two colors, comprising: an iterative spectrum combiner, configured to iteratively combine a first spectrum representative of a first color in the hair mixture from a first group of spectrums and a second spectrum representative of a second color in the hair mixture from a second group of spectrums into an optimized spectrum including a respective concentration of each of the first spectrum and second spectrum, the iterative spectrum combiner being further configured to calculate the concentrations to optimize fitness of the optimized spectrum to the overall spectrum; and a fitness optimizer, associated with the spectrum selector and spectrum calculator, configured to find among the optimized spectrums an optimized spectrum best fitting the overall spectrum.

According to a third aspect of the present invention there is provided an apparatus for analyzing a sample hair mixture having a mixture of two hair colors and an overall spectrum representative of the two colors, comprising: a spectrum selector, configured to select a spectrum of colored hair such that the spectrum best fits the overall spectrum among a plurality of colored hair spectrums; and a curvature comparator, associated with the spectrum selector and configured to compare curvature of the selected spectrum with curvature of the overall spectrum and to determine concentration of white hair in the hair mixture according to the curvature comparison.

According to a fourth aspect of the present invention there is provided a method for analyzing a sample hair mixture having a mixture of two hair colors and an overall spectrum representative of the two colors, comprising: iteratively performing the steps of a) selecting a first spectrum representative of a first color in the hair mixture from a first group of spectrums; b) selecting a second spectrum representative of a second color in the hair mixture from a second group of spectrums; c) calculating an optimized spectrum based on the first spectrum, the second spectrum, and a respective concentration of each of the first spectrum and second spectrum, the concentrations calculated to optimized fitness of the optimized spectrum to the overall spectrum; until finding an optimized spectrum best fitting the overall spectrum.

According to a fifth aspect of the present invention there is provided a method for analyzing a sample hair mixture having a mixture of two hair colors and an overall spectrum representative of the two colors, comprising: selecting a spectrum representative of colored hair such that the spectrum best fits the overall spectrum among a plurality of colored hair spectrums; comparing curvature of the overall spectrum with curvature of the selected spectrum; finding a concentration of white hair color in the hair mixture according to the curvature comparison.

According to a sixth aspect of the present invention there is provided a method of dying hair having a mixture of two hair colors and an overall spectrum representative of the two colors, comprising: iteratively performing the steps of a) selecting a first spectrum representative of a first color in the hair mixture from a first group of spectrums; b) selecting a second spectrum representative of a second color in the hair mixture from a second group of spectrums; c) calculating an optimized spectrum based on the first spectrum, the second spectrum, and a respective concentration of each of the first spectrum and second spectrum, the concentrations calculated to optimized fitness of the optimized spectrum to the overall spectrum; until finding an optimized spectrum best fitting the overall spectrum, and prescribing a hair dyeing treatment according to the found optimized spectrum.

According to a seventh aspect of the present invention there is provided a method of selecting dye ingredients for dyeing hair having a mixture of two hair colors and an overall spectrum representative of the two colors, comprising: iteratively performing the steps of a) selecting a first spectrum representative of a first color in the hair mixture from a first group of spectrums; b) selecting a second spectrum representative of a second color in the hair mixture from a second group of spectrums; c) calculating an optimized spectrum based on the first spectrum, the second spectrum, and a respective concentration of each of the first spectrum and second spectrum, the concentrations calculated to optimized fitness of the optimized spectrum to the overall spectrum, until finding an optimized spectrum best fitting the overall spectrum, and prescribing ingredients for a hair dyeing treatment according to the found optimized spectrum.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified block diagram illustrating a first apparatus for analyzing a sample hair mixture having a mixture of two hair colors, according to a preferred embodiment of the present invention;

FIG. 2 is a simplified block diagram illustrating a second apparatus for analyzing a sample hair mixture having a mixture of two hair colors, according to a preferred embodiment of the present invention;

FIG. 3 is a simplified block diagram illustrating a third apparatus for analyzing a sample hair mixture having a mixture of two hair colors, according to a preferred embodiment of the present invention;

FIG. 4 is a simplified flowchart illustrating a first method for analyzing a sample hair mixture of two hair colors and an overall spectrum representative of the two colors, according to a preferred embodiment of the present invention;

FIG. 5 is a flowchart illustrating a second method for analyzing a sample hair mixture of two hair colors and an overall spectrum representative of the two colors, according to a preferred embodiment of the present invention;

FIG. 6 is a simplified flowchart illustrating a third method for analyzing a sample hair mixture of two hair colors and an overall spectrum representative of the two colors, according to a preferred embodiment of the present invention;

FIG. 7 is a flowchart illustrating a fourth method for analyzing a sample hair mixture of two hair colors and an overall spectrum representative of the two colors, according to a preferred embodiment of the present invention;

FIG. 8 is simplified flowchart illustrating a fifth method for analyzing a sample hair mixture of two hair colors and an overall spectrum representative of the two colors, according to a preferred embodiment of the present invention;

FIG. 9 is a detailed flowchart illustrating a sixth method for analyzing a sample hair mixture of two hair colors and an overall spectrum representative of the two colors, according to a preferred embodiment of the present invention;

FIG. 10 is a line graph illustrating spectrums of exemplary hair samples;

FIG. 11 is a line graph illustrating a hair sample mixture spectrum vs. a closely fitted natural spectrum;

Figure 12:
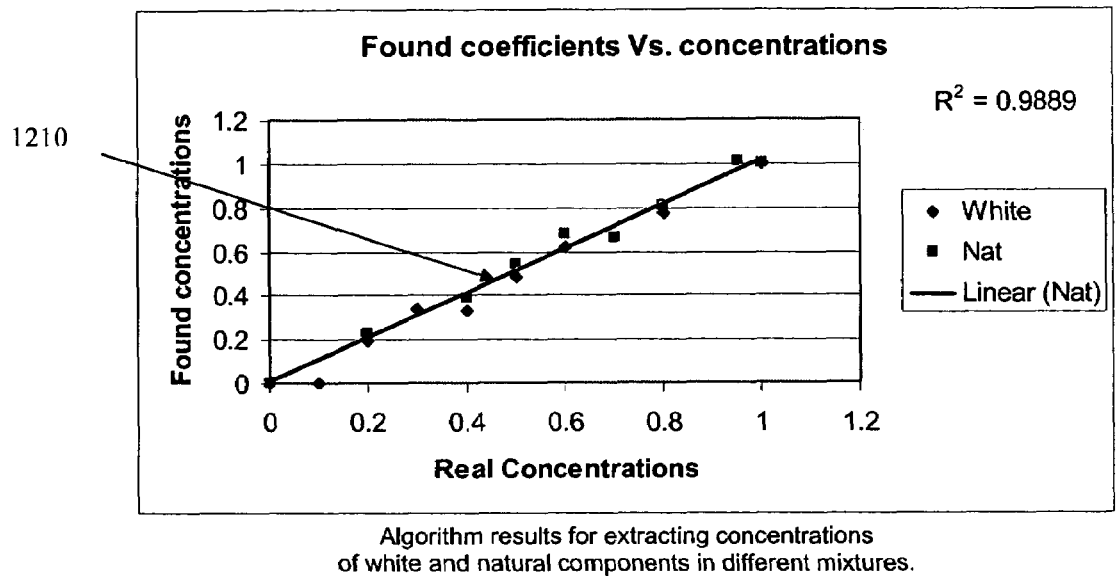
Figure 13:
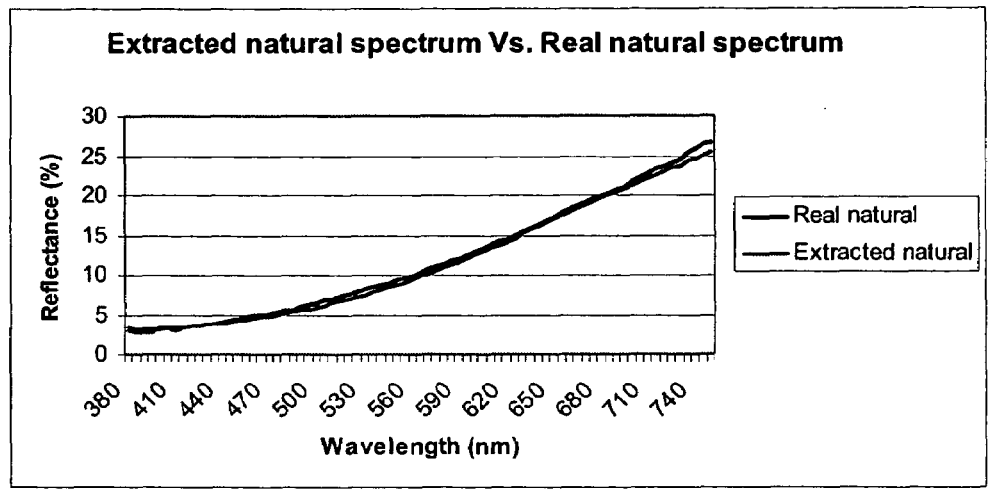
Figure 14:
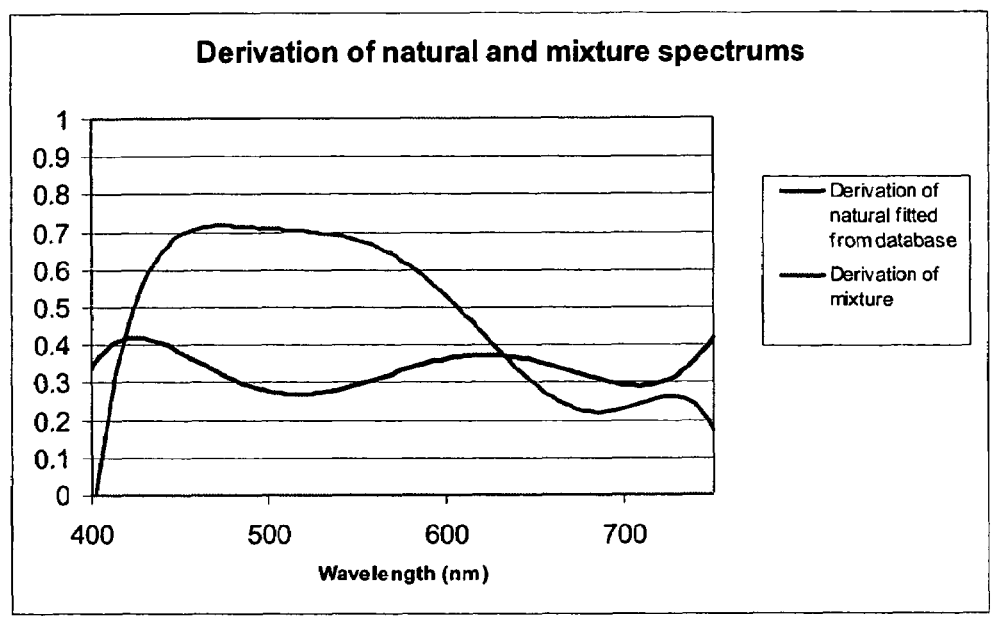

FIG. 12 is a line graph illustrating resultant correlation between extracted concentrations and real concentrations of hair color in different mixtures;

FIG. 13 is a line graph illustrating a comparison between an extracted natural hair spectrum and the real spectrum; and FIG. 14 is a line graph illustrating curvature differences between a natural spectrum and a sample hair mixture spectrum.

DESCRIPTION OF THE PREFERRED EMBODIMENTS

The present embodiments comprise an apparatus and a method for analyzing a sample hair mixture having a mixture of hair colors.

The principles and operation of an apparatus and a method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to a preferred embodiment of the present invention there is provided a method and an apparatus for analyzing a given reflectance spectrum of a hair sample which may be comprised of a mixture of natural hair and white hair. The analysis separately considers the pure spectrums of the natural and white hair and then combines them, also defining the concentrations of each of them in the mixture.

A preferred embodiment of the present invention utilizes pre-constructed databases: a database of colored hair reflectance spectrums and a database of white hair reflectance spectrums. The colored hair database covers the spectral space of dyed and natural colored hair. In an embodiment the dyed spectrums are filtered out. This colored database does not include white hair. The white hair database contains the reflectance spectrums of different variations of white hair.

Given a reflectance spectrum of a hair mixture that contains colored and white hairs, the method performs a database search in order to find the spectrums that best fit (say, according to RMS value as described in greater detail herein below) to the colors and white hair spectrums. The method then preferably finds the concentration of each of the colors in the mixture.

Figure 1:
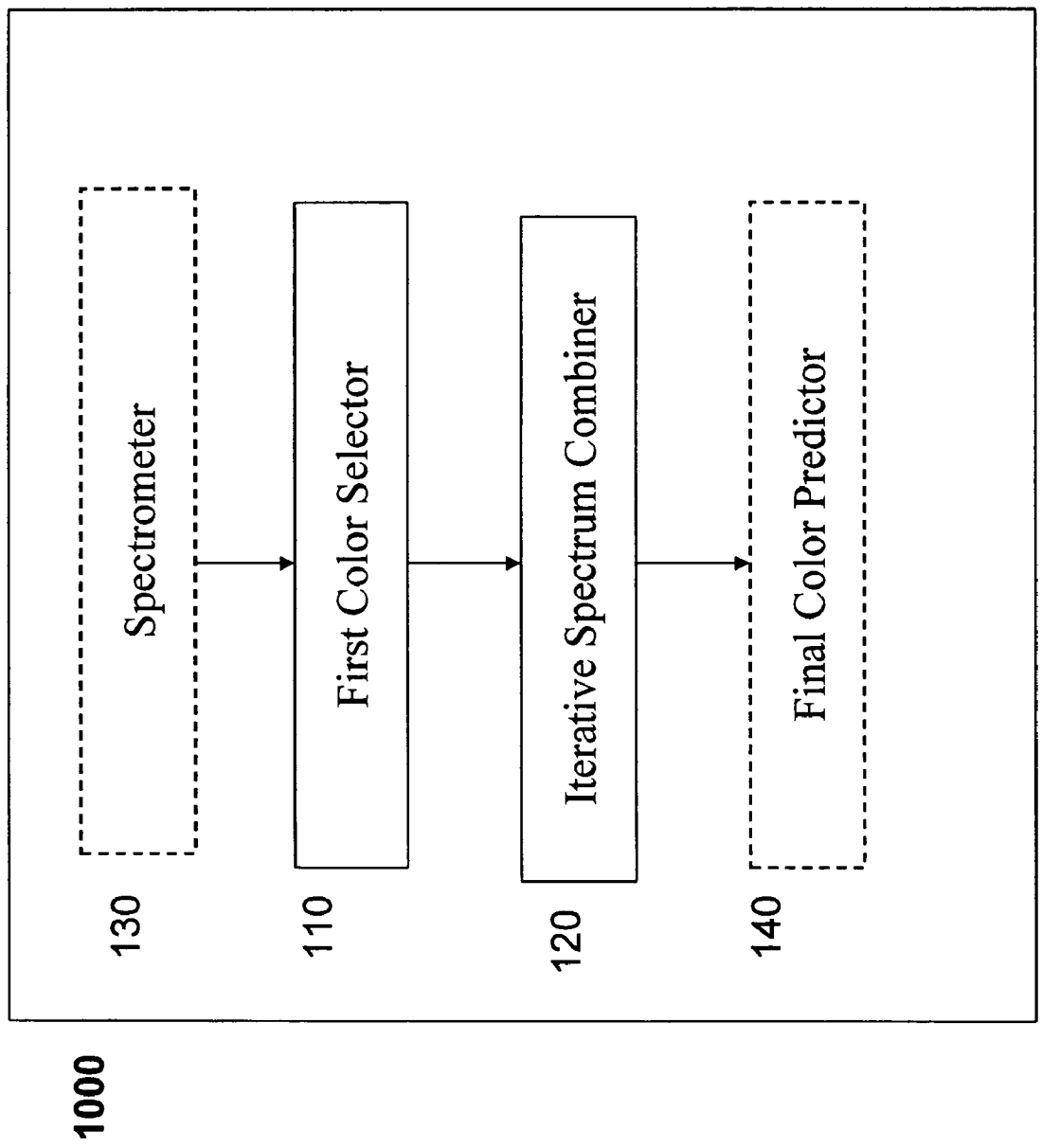

Reference is now made to FIG. 1, which is a simplified block diagram illustrating a first apparatus for analyzing a sample hair mixture having a mixture of two hair colors, according to a preferred embodiment of the present invention.

An apparatus 1000 according to. a preferred embodiment of the present invention includes a first color selector 110.

The first color selector 110 is used to select a first spectrum representing one of the colors in the sample from a first group which includes one or more white hair spectrums. Optionally the first group consists of one or more white hair reflectance spectrums, stored in a white hair database, as described hereinabove.

The apparatus 1000 further includes an iterative spectrum combiner 120.

The iterative spectrum combiner 120 iteratively combines a second spectrum to the first spectrum. The second spectrum represents a second color in the sample hair mixture and is selected from a second group of hair color spectrums. Through iteratively combing a second spectrum to the first spectrum, the iterative spectrum combiner 120 finds an optimal combination. The optimal combination is the combination having a spectrum closest matching an overall measured spectrum representative of the sample hair mixture.

Preferably, the iterative spectrum combiner 120 is further configured to find the optimal combination by finding the concentrations of the hair colors in the current combination which optimize the match between the current combination's spectrum and the overall spectrum of the hair mixture sample.

Optionally, the second group of hair color spectrums consists of one or more natural or dyed hair spectrums. Optionally, the natural or dyed hair color spectrums of the second group are pre-stored in a database, as described hereinabove.

Optionally, the matching of the current combination with the overall spectrum is determined by the iterative spectrum combiner 120 according to a measurement of difference between the spectrum of the combination and the overall spectrum.

The measurement of difference between the spectrum of the combination and the overall spectrum may be based on root mean square (RMS) difference measurement between the combination's spectrum and the overall spectrum, using the methods described in detail herein below, or according to any other known in art method such as a pattern recognition technique, etc.

Preferably, the RMS difference measurement is carried out for a group of ten or more points on each spectrum, thus basing the RMS measurement on a discrete but near continuous part of the spectrum. In a preferred embodiment, the RMS difference measurement is carried out for a group of up to seventy five points on each spectrum. In one preferred embodiment the continuous spectrum that is produced is sampled between wavelengths of 380 nm and 780 nm with a resolution of 5 nanometers.

Preferably, the apparatus 1000 further comprises a spectrometer 130, connected to the first color selector 110, for obtaining the overall spectrum of the sample.

The spectrometer 130 may be any relevant known in the device which is usable for measuring absorption and attenuation in the hair sample as a function of different wavelengths of light.

For example, U.S. patent application Ser. No. 10/473,627, entitled "Hair color measurement and treatment", to Grossinger et al, filed on Oct. 1, 2003, which is hereby incorporated by reference, introduces a spectrometer for producing a usable reflectance spectrum of hair without having to remove the hair sample from the head of the customer.

More preferably, the apparatus 1000 further includes a final color predictor 140 which may be configured to predict a spectrum of a final hair mixture resulting upon applying a dyeing color to the hair mixture, as described in greater detail herein below.

Preferably, the predicted spectrum may be visually presented to a client prior to dyeing his hair, say as an image representative of his hair appearance upon dyeing with the dyeing color.

Figure 2:
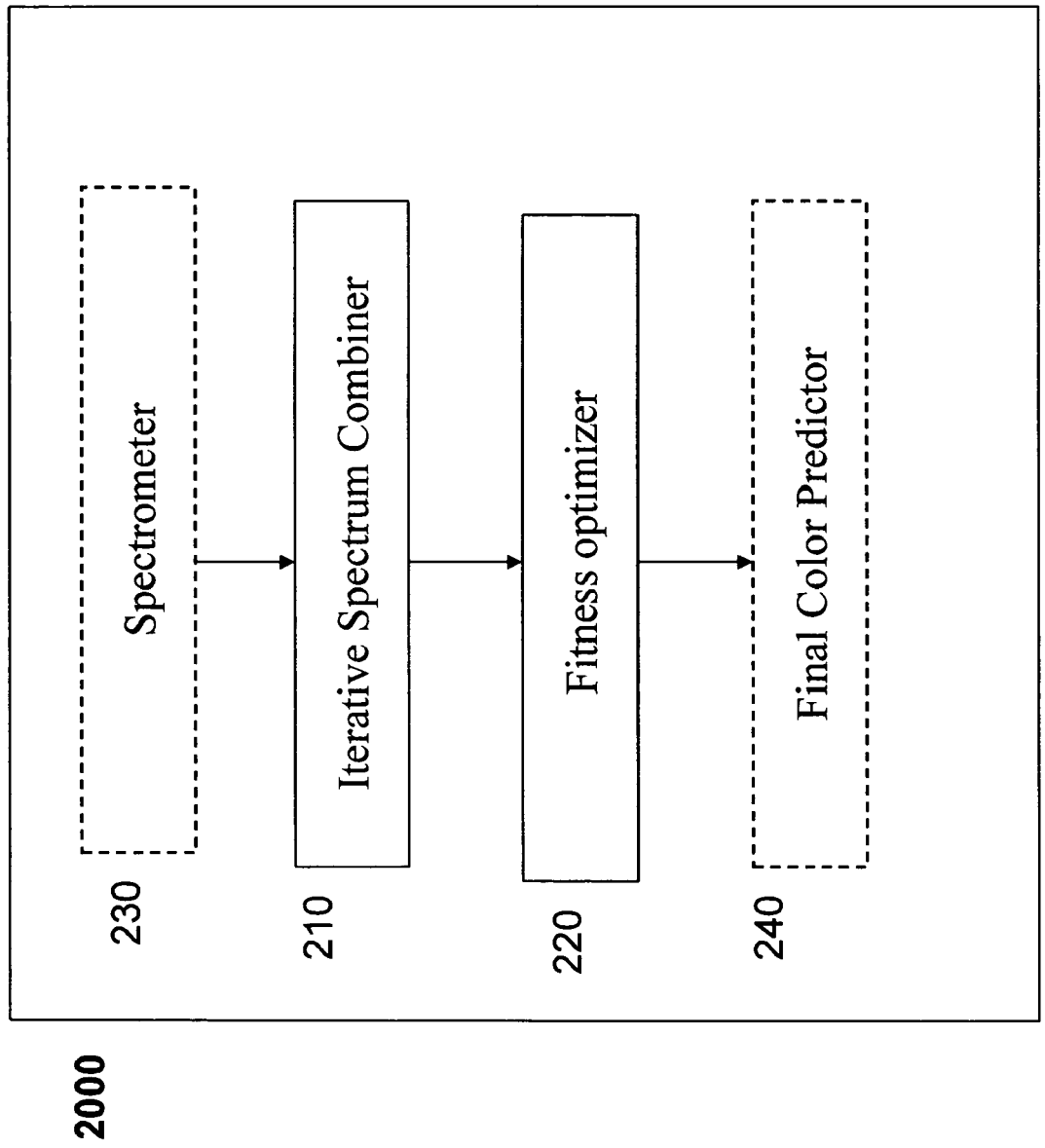

Reference is now made to FIG. 2, which is a simplified block diagram illustrating a second apparatus for analyzing a sample hair mixture having a mixture of two hair colors, according to a preferred embodiment of the present invention.

An apparatus 2000 according to a preferred embodiment of the present is used to analyze a sample hair mixture having a mixture of two hair colors and an overall spectrum representative of the two colors.

The apparatus 2000 includes an iterative spectrum combiner 210.

The iterative spectrum combiner 210 iteratively combines a spectrum representative of a first color in the sample hair mixture and a spectrum of representative of a second color in the sample hair mixture. The first group consists of different white hair color spectrums. The second spectrum is selected from a second group of natural hair color spectrums. The second group includes one or more natural and dyed hair colors.

Preferably, the first group is pre-stored in a database of natural or color hair reflectance spectrums, and the second group is pre-stored in a database of white hair reflectance spectrums. Preferably, the natural hair database significantly covers the spectral space of uncolored hair.

Optionally, the natural hair database does not include white hair and is filtered out of hair samples that are suspected to be dyed, for creating a pure natural hair database. The white hair database contains the reflectance spectrums of different variations of white hair.

The iterative spectrum combiner 210 is further configured to calculate an optimal concentration for the first color and an optimal concentration for the second color.

The optimal concentrations optimize fitness of the spectrum representing the combination of the two colors, such that the resultant optimized spectrum is closest fitting to the overall spectrum of the sample hair mixture. The calculation of the optimal concentration may be carried out utilizing the below described methods.

The apparatus 2000 further includes a fitness optimizer 220.

The fitness optimizer 220 is connected to the iterative spectrum combiner 210 and configured to find among the optimized spectrums an optimized spectrum best fitting the overall spectrum of the hair mixture sample.

The fitting of a spectrum to the overall spectrum may be determined according to a root mean square (RMS) difference measurement between the spectrum and the overall spectrum of the hair mixture sample, using the methods described in detail herein below, or by any other known in art method such as a pattern recognition technique, etc.

Preferably, the apparatus 2000 further comprises a spectrometer 230, connected to the iterative spectrum combiner 110, for obtaining the overall spectrum of the sample.

The spectrometer 230 may be any relevant known in the art device which is usable for measuring absorption and attenuation in the hair sample as a function of different wavelengths of light.

For example, U.S. patent application Ser. No. 10/473,627, entitled "Hair color measurement and treatment", to Grossinger et al, filed on Oct. 1, 2003, which is hereby incorporated by reference, introduces a spectrometer for producing a usable reflectance spectrum of hair without having to remove the hair sample from the head of the customer, as discussed hereinabove.

More preferably, the apparatus 2000 further comprises a final color predictor 240.

The final color predictor 240 is configured to predict a spectrum of a final hair mixture, resultant upon applying a dyeing color to the hair mixture, as described in greater detail herein below.

Preferably, the predicted spectrum may be visually presented to a client prior to dyeing his hair, say as an image representative of his hair appearance upon dyeing with the dyeing color, as discussed hereinabove.

Figure 3:
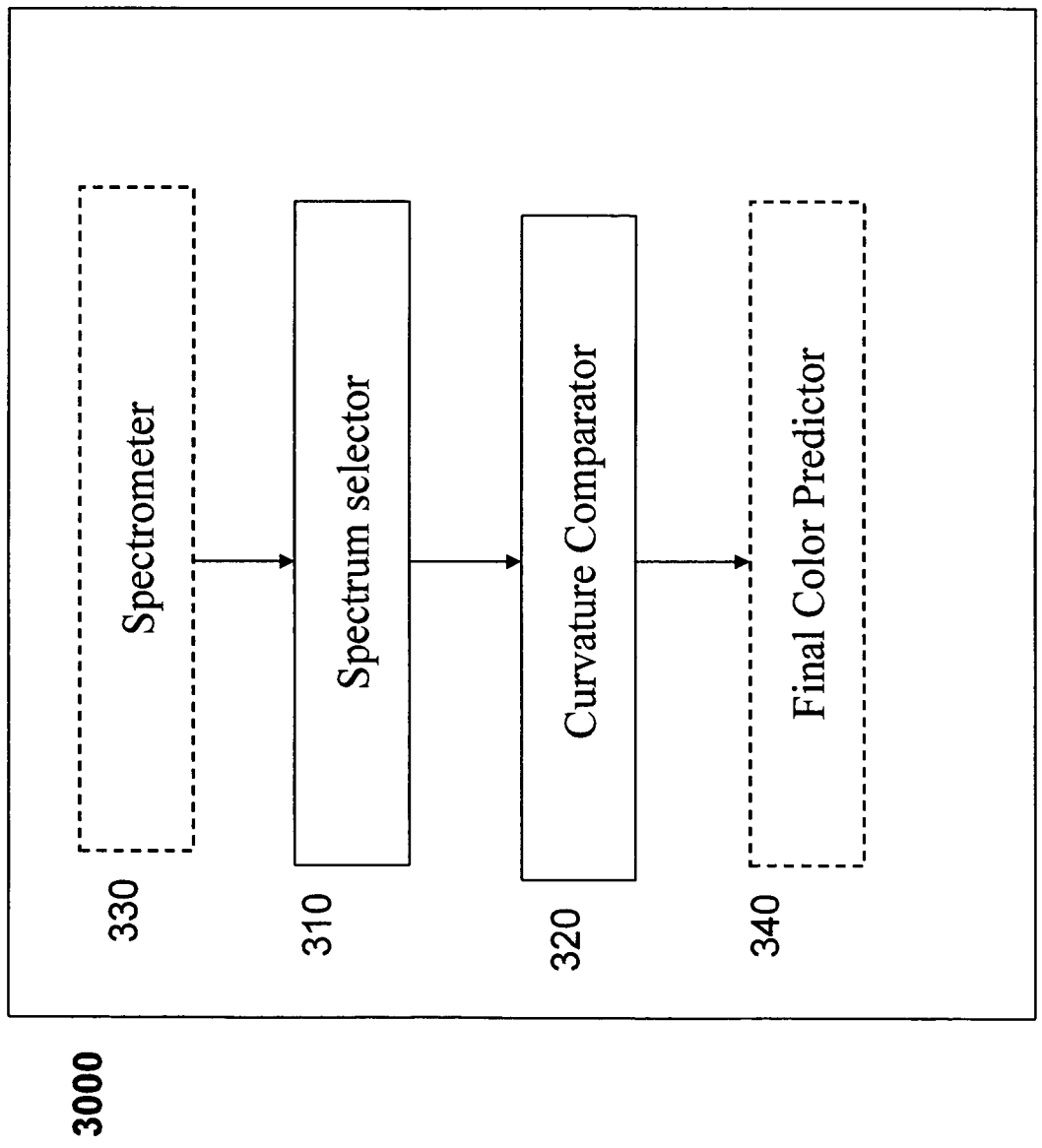

Reference is now made to FIG. 3, which is a simplified block diagram illustrating a third apparatus for analyzing a sample hair mixture having a mixture of two hair colors, according to a preferred embodiment of the present invention.

An apparatus 3000 for analyzing a sample hair mixture having a mixture of two hair colors and an overall spectrum according to a preferred embodiment of the present invention includes a spectrum selector 310.

The spectrum selector 310 is used to select a spectrum of natural hair color, best fitting the overall spectrum from a group of natural hair color spectrums. Preferably, the group of hair color spectrums is pre-stored in a database, as described hereinabove.

The spectrum selector 310 is further configured to determine the fitness of a spectrum to the overall spectrum of the sample according to any currently known technique, including but not limited to a root mean square (RMS) measurement of difference between the spectrum and the overall spectrum of the hair mixture sample, as implemented by the methods described in detail below.

The apparatus 3000 further includes a curvature comparator 320.

The curvature comparator 320 is connected to the spectrum selector 310 and configured to find the curvature of the reflectance spectrum of the sample as calculated by a derivation of a mathematical function representative of the selected spectrum.

The curvature comparator 320 is further configured to compare the curvature of the selected spectrum with the curvature of the overall spectrum of the sample hair mixture.

In general, a white hair spectrum has a much lower curvature than natural hair. This curvature difference is most significant in the wavelength range of 460-570 nm. In a mixed sample of white and natural hair the curvature of the spectrum ranges between standard natural spectrum curvature for a pure natural sample and standard white spectrum curvature for a pure white sample. The curvature of the spectrum varies between those two edges with correlation to the concentration of the white hair and natural hair components in the mixture.

The curvature comparator 320 is thus configured to determine the existence or concentration of white hair in the hair mixture according to the curvature comparison between the selected spectrum and the overall spectrum of the sample hair mixture, as described in greater detail herein below.

Preferably, the apparatus 3000 further comprises a spectrometer 330, connected to the spectrum selector 310, for obtaining the overall spectrum of the sample, as described in greater detail hereinabove.

More preferably, the apparatus 3000 further comprises a final color predictor 340 predicts a spectrum of a final hair mixture resultant upon applying a dyeing color to the hair mixture, as described in greater detail herein below.

Preferably, the predicted spectrum may be visually presented to a client prior to dyeing his hair, say as an image representative of his hair appearance upon dyeing with the dyeing color, as discussed hereinabove.

Before describing methods implemented by the above described apparatuses according to a preferred embodiment of the present invention, a description of dependencies of colored, white and mixture spectrums is provided in the following paragraphs.

The intensity change of light that travels in an absorbing material is described by Beer's law as:

$$I_{output} = I_{input} \cdot e^{-\alpha \cdot coeff \cdot l}$$

Where $I_{input}$ is the input intensity, $\alpha$ is the absorbing characteristic of the material and Coeff represents the concentration of material (the propagation length of light l in the sample is approximated as constant for all hair samples and is not referenced further on). Any additional absorbing material added is added in multiplicative manner. In this case the output intensity measured is the reflectance spectrum and therefore: $I_{output} = R_f$.

In the case of a mixture of colored and white hair we may consider the colored hair absorbance and the white hair absorbance to be the fundamental absorbance components in the mixture. Therefore the reflectance spectrum of the mixture can be represented as:

$$R_{Mixture_\lambda} = I_{input_\lambda} \cdot e^{-\alpha Natural \lambda \cdot Coeff_{Natural}} \cdot e^{-\alpha White \lambda \cdot Coeff_{White}}.$$

Since the sum of the components concentrations equals to 1 then:

$$R_{Mixture} = (I_{input} \cdot e^{-\alpha Natural})^{Coeff_{Natural}} \cdot (I_{input} \cdot e^{-\alpha White})^{Coeff_{White}}$$

hence $$R_{Mixture_\lambda} = (R_{Natural_\lambda})^{Coeff_{Natural}} \cdot (R_{White_\lambda})^{Coeff_{White}} \quad \text{(Equation 1.1)}$$

Where:

$R_{Mixture}$, $R_{Natural}$, $R_{White}$ are the reflectance spectrums of the mixture, colored and white hairs respectively;

and $Coeff_{Natural}$, $Coeff_{White}$ are the concentrations of the colored and white hairs in the mixture.

Equation 1.1 presents a way of describing the dependency of the mixture reflectance spectrum with the colored and white hair spectrums and the color's concentrations in the mixture.

The spectrums that are most similar (i.e. have the smallest RMS value) to the true spectrums of the colored and white hair in the mixture construct a spectrum with the smallest RMS value to the measured mixture spectrum when putting the right coefficients.

That is to say that an optimal spectrum constructed from a first color spectrum selected from a database of colored hair color spectrums and a second color spectrum selected from a database of white hair color spectrums has a minimal RMS value, indicating a closest fitting with the overall spectrum of the hair mixture sample when the two colors are taken in the optimal concentrations, as indicated by the coefficients.

Figure 4:
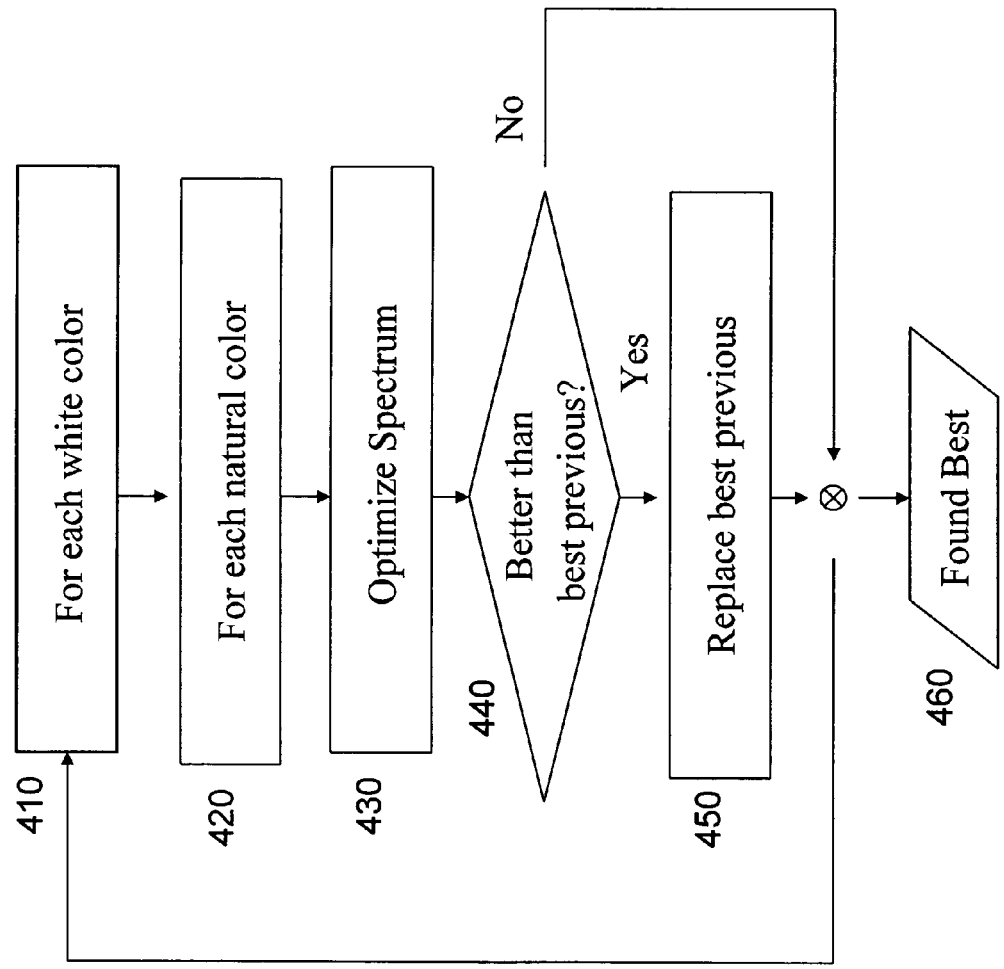

Reference is now made to FIG. 4, which is a simplified flowchart illustrating a first method for analyzing a sample hair mixture of two hair colors and an overall spectrum representative of the two colors, according to a preferred embodiment of the present invention.

Given a reflectance spectrum of a mixture of white and colored hair, a database of white hair spectrums and a database of colored hair spectrums, a first method according to a preferred embodiment of the present invention implements the following logic:

For each white spectrum in the white hair database 410, iterate through each colored spectrum in the colored hair database 420 and optimize the spectrum resultant upon combining the white and colored spectrums 430.

For example, the optimized spectrum may be found using equation 1.1, by finding 430 the colored and white coefficients ($Coeff_{Natural}$, $Coeff_{White}$) for an optimized spectrum which results when combining the colored and white spectrums, while keeping the sum of the coefficients equals to 1.

If the optimized spectrum is better than the best optimized spectrum among previous ones 440, the optimized spectrum replaces the previously best optimized spectrum 450.

Finally, after iterating through all combinations of white and colored color spectrums, the best optimized spectrum is found 460.

Figure 5:
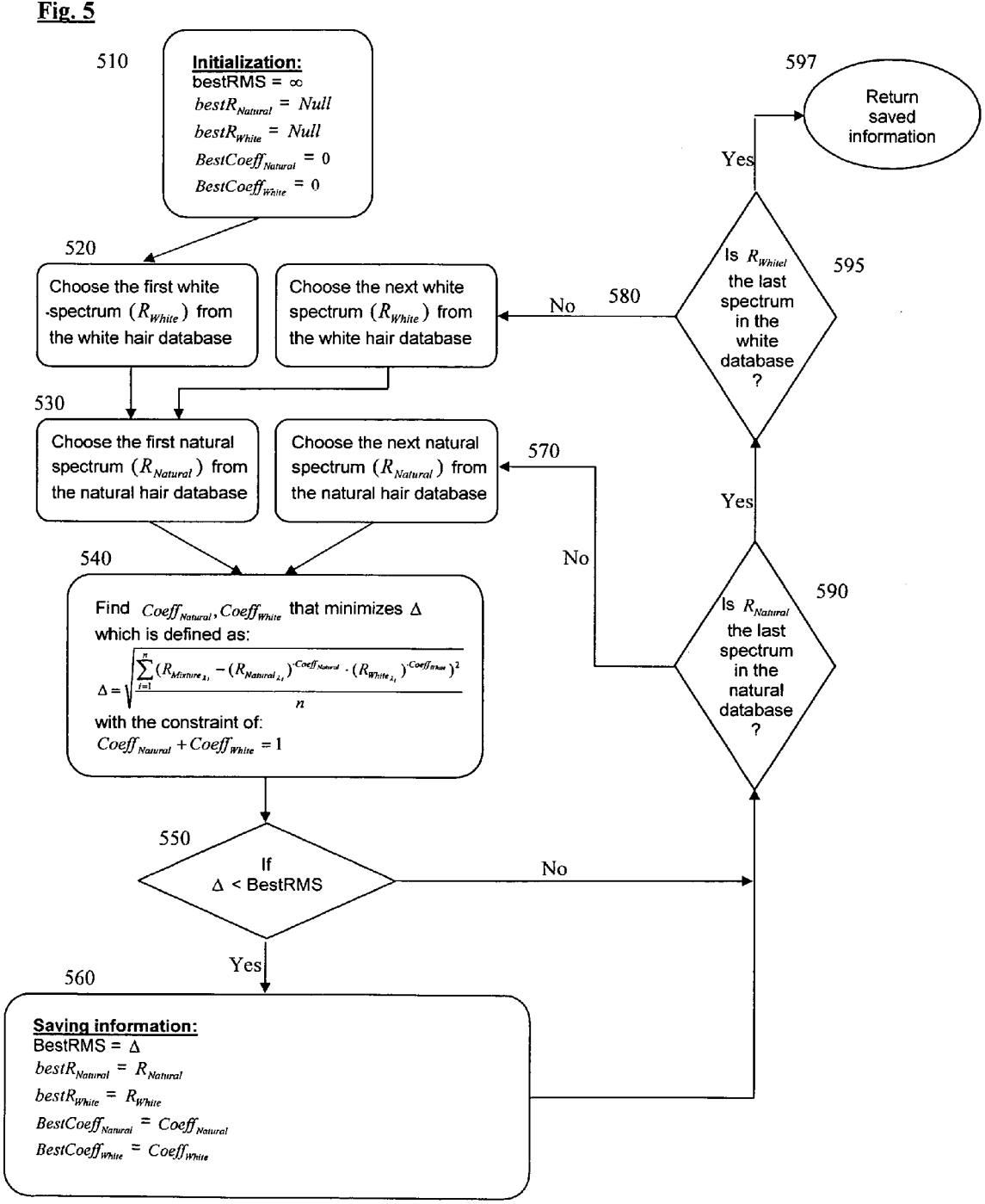

Reference is now made to FIG. 5, which is a flowchart illustrating a second method for analyzing a sample hair mixture of two hair colors and an overall spectrum representative of the two colors, according to a preferred embodiment of the present invention.

A detailed example of the above described first method that may be implemented by an apparatus according to a preferred embodiment of the present invention includes the following steps:

At an initiation stage 510, parameters relating to the best fitting are initialized.

Next, a white hair color spectrum is selected from a white hair database 520.

Then, a first colored spectrum is selected from the colored hair database 530.

Next, the two current spectrums are combined and an optimization is made 540 with regard to a spectrum which is representative of the combination of the two spectrums. The optimization is made by finding a concentration of each of the two spectrums such that the distance between the overall spectrum of the hair mixture sample and the spectrum which is representative of the combination of the two spectrums is the smallest possible, given the two selected spectrums.

Optionally, the optimization 540 is made by minimization of a RMS value indicating the difference between the spectrum of the combination and the overall spectrum of the hair mixture sample, say using the mathematical provided formula 540.

The optimization is carried out by finding a coefficient values combination which minimizes the RMS value. One of the coefficients indicate concentration of the first color, and the other coefficient indicates the concentration of the second color. A constraint is made keeping the sum of the coefficients equal to one.

Then, the optimized spectrum is compared to best RMS value found 550 for the best among previously optimized spectrums. If the optimized spectrum is better than previously reached optimized spectrums, that is to say having a smaller RMS value, the best optimized spectrum parameters are updated 560 according to the parameters of the optimized spectrum.

If there are other colored spectrums 590 to combine with the white hair spectrum, a next colored spectrum is selected from the colored hair spectra database 570, for producing a new optimized spectrum and comparing the spectrum with previous ones, as described hereinabove.

Optionally, if the there are no other colored spectrums in the colored spectra database but more white spectrums left in the white spectra database 595, then a next white spectrum is selected from the colored hair spectra database 580, for producing a new optimized spectrum and comparing the spectrum with previous ones, as described hereinabove. A preferred embodiment uses only a single white spectrum.

Finally, when neither a white spectrum nor a colored spectrum is left, the information relating to the best optimized spectrum reached throughout the iterative method is returned 597.

A second variation of the above described methods is to look for the spectrums that construct the mixture spectrum with a RMS value that is less than one and choose from them the ones that use coefficients with a sum closest to one, as illustrated using FIG. 6 herein below.

Figure 6:
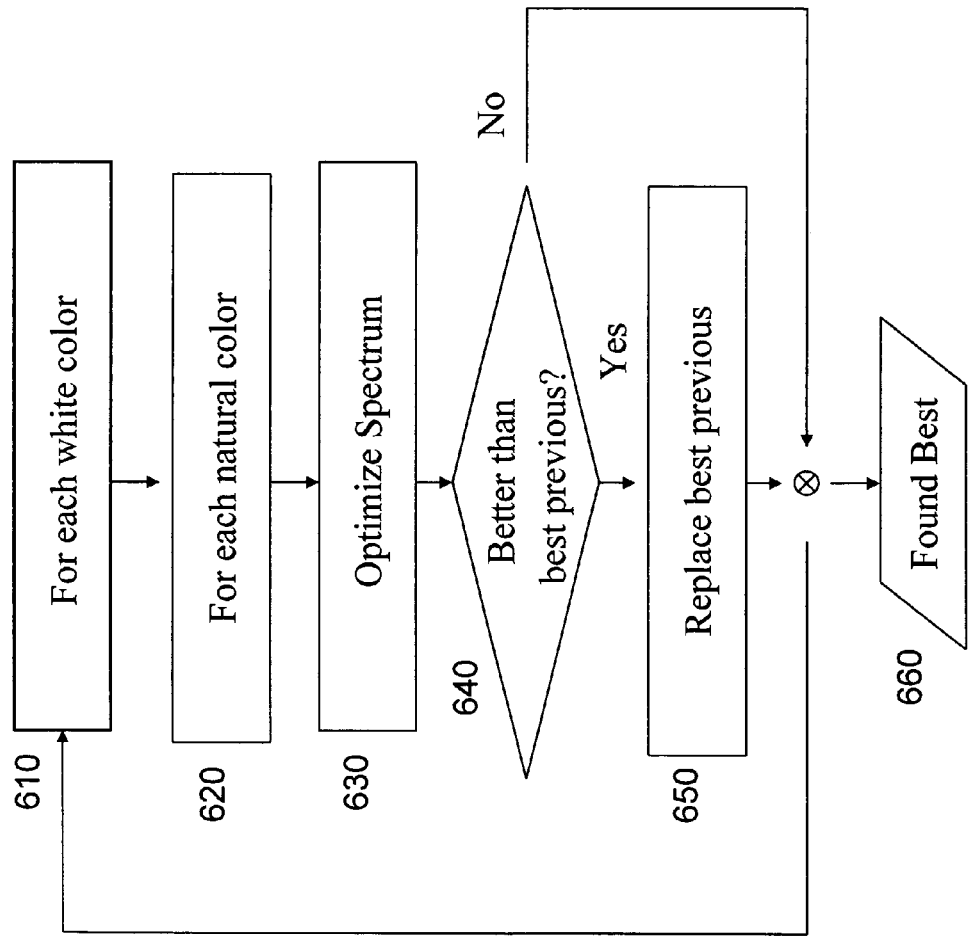

Reference is now made to FIG. 6, which is a simplified flowchart illustrating a third method for analyzing a sample hair mixture of two hair colors and an overall spectrum representative of the two colors, according to a preferred embodiment of the present invention.

Given a reflectance spectrum of a mixture of white and colored hair, a database of white hair spectrums and a database of colored hair spectrums, a first method according to a preferred embodiment of the present invention implements the following logic:

For each white spectrum in the white hair database 610, iterate through each colored spectrum in the colored database 620.

Optimize the spectrum of the combined white and colored spectrums, say by performing a non negative least squares 630 minimization with the white, colored and mixture spectrums using equation 1.1. Using equation 1.1, the colored and white coefficients that optimize the fitness of the combination to the overall spectrum of the sample hair mixture are found.

Find if the optimized spectrum is better than the best among previously optimized spectrums 640.

If the optimized spectrum is better than the previously found best combination's spectrum, say if the RMS value between the constructed spectrum and the mixture spectrum is less than one and the sum of the colored and white coefficients are the closer to one from the previous results than save the current colored spectrum, white spectrum and the colored and white coefficients 650 describing the constructed spectrum.

After iterating through all combinations of white and colored color spectrums, the saved colored spectrum, white spectrum, and the colored and white coefficients describing the optimized spectrum best matching the overall spectrum of the hair mixture sample is finally found 660.

Figure 7:
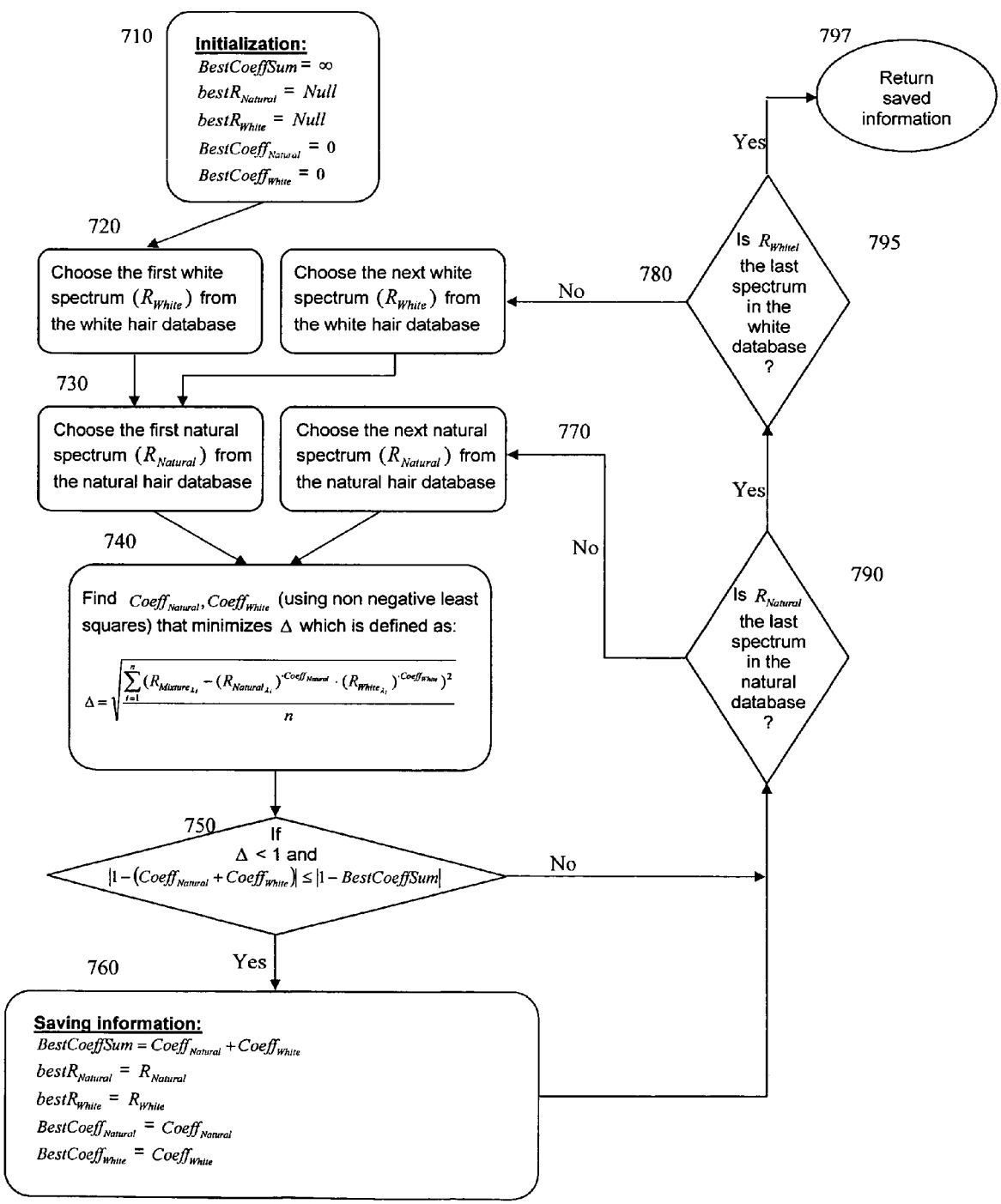

Reference is now made to FIG. 7, which is a flowchart illustrating a fourth method for analyzing a sample hair mixture of two hair colors and an overall spectrum representative of the two colors, according to a preferred embodiment of the present invention.

A detailed example of the above described third method that may be implemented by an apparatus according to a preferred embodiment of the present invention includes the following steps:

At an initiation stage 710, parameters relating to the best fitting are initialized. Next, a white hair color spectrum is selected from a white hair database 720. Then, a first colored spectrum is selected from the colored hair database 730.

Next, an optimization is made 740 with regard to a spectrum which is representative of the combination of the two colors. Optionally, the optimization is made by minimization of an RMS value indicating the difference between the spectrum of the combination and the overall spectrum of the hair mixture sample.

The optimization is carried out using non negative least squares with the white, colored and mixture spectrums using equation 1.1, in order to find the colored and white coefficients that optimize the fitness of the combination to the overall spectrum of the sample, without restricting the sum of the coefficients to one. One of the coefficients indicates concentration of the first color, and the other coefficient indicates the concentration of the second color.

Then, the optimized spectrum is compared to best RMS value found 750 for previous optimized spectrums. If the RMS value is between the constructed spectrum and the overall spectrum of the hair mixture sample is less than one and the sum of the colored hair and white hair coefficients is closer to one then those of the previously found best spectrum, then the parameters of the constructed spectrum are saved 760 as the parameters of the best spectrum.

If there are other colored spectrums 790 to combine with the white hair spectrum, a next colored spectrum is selected from the colored hair spectra database 770, for producing 740 a new optimized spectrum. The new optimized spectrum is compared with the best among previously found optimized spectrums 750, and if found better, the new optimized spectrum replaces the previous one 760, as described hereinabove.

If the there are no other colored spectrums in the colored spectra database but more white spectrums left in the white spectra database 795, then a next white spectrum is selected from the colored hair spectra database 780, for producing a new optimized spectrum and comparing the spectrum with the best among previous ones, as described hereinabove.

When no other spectrums white or colored are left, the information relating to the best optimized spectrum reached throughout the iterative method is returned 597.

Another approach for detecting white hair in a hair sample is to use the curvature of the reflectance spectrum of the sample. As described hereinabove, in general, a white hair spectrum has a much lower curvature than colored hair. This curvature difference is most significant in the wavelength range of 460-570 nm. In a mixed sample of white and colored hair the curvature of the spectrum ranges between standard colored spectrum curvature for a pure colored sample and a standard white spectrum curvature for a pure white sample. The curvature of the spectrum varies between those two edges with correlation to the concentration of the white hair and colored hair components in the mixture.

According to a preferred embodiment of the present invention, the detection of white hair in a given hair sample is done using a database of colored hair spectrums. The database is used to find the reflectance spectrum that is most similar to the given spectrum. Then, the curvature of the overall spectrum of the sample of hair mixture is compared to the curvature of the reflectance spectrum found in the database.

Figure 8:
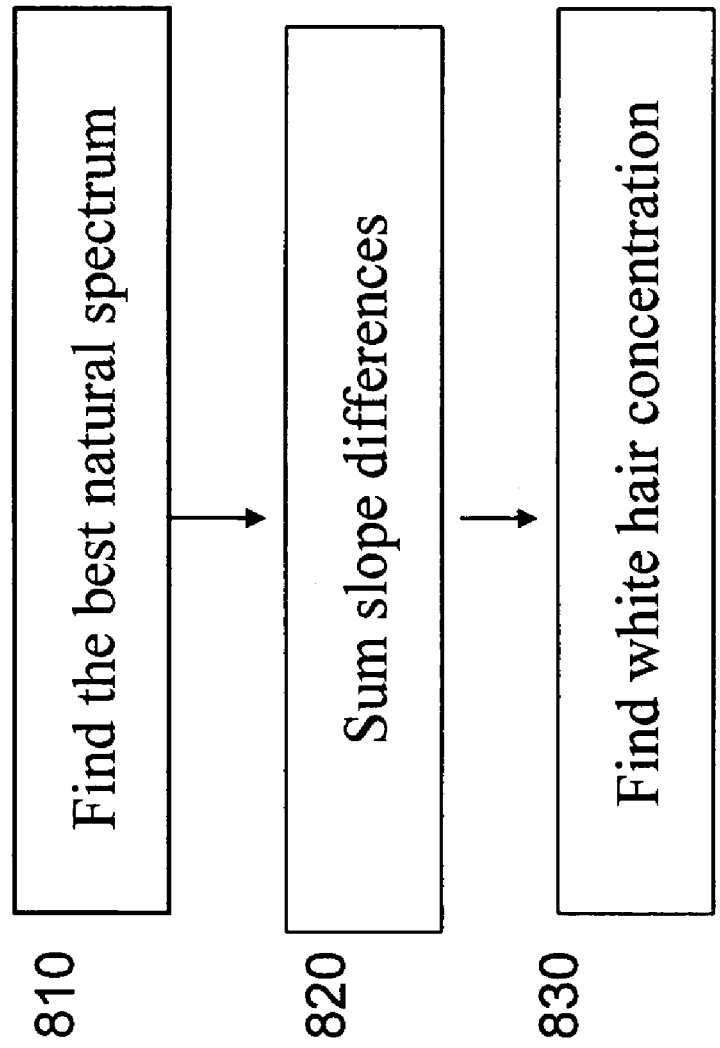

Reference is now made to FIG. 8 which is simplified flowchart illustrating a fifth method for analyzing a sample hair mixture of two hair colors and an overall spectrum representative of the two colors, according to a preferred embodiment of the present invention.

Given a hair sample and a database of colored spectrums, a method according to a preferred embodiment of the present invention includes the following steps:

Find the colored spectrum in the database which best fits the overall spectrum of the hair mixture sample. For example, with RMS minimization, the lower is the RMS value to the overall spectrum 810, the greater is the fitness between the found spectrum and the overall spectrum of the hair mixture sample.

Calculate the slope 820 at different wavelengths of the given sample's overall reflectance spectrum and the slope at the same wavelengths of the spectrum found in the database, and sum the differences between the slopes of the found database spectrum and the overall spectrum at each of the wavelength. Preferably, all the wavelengths are in the range of 460-570 nm where the difference of slopes is likely to be more significant.

For colored hair sample, the sum of the slopes differences is around zero. However, a sum which is greater than zero indicates the existence of white hair in the sample. The slopes difference is correlated with the concentration of the white hair in the mixture and may thus be used as an indication for the concentration 830.

Figure 9:
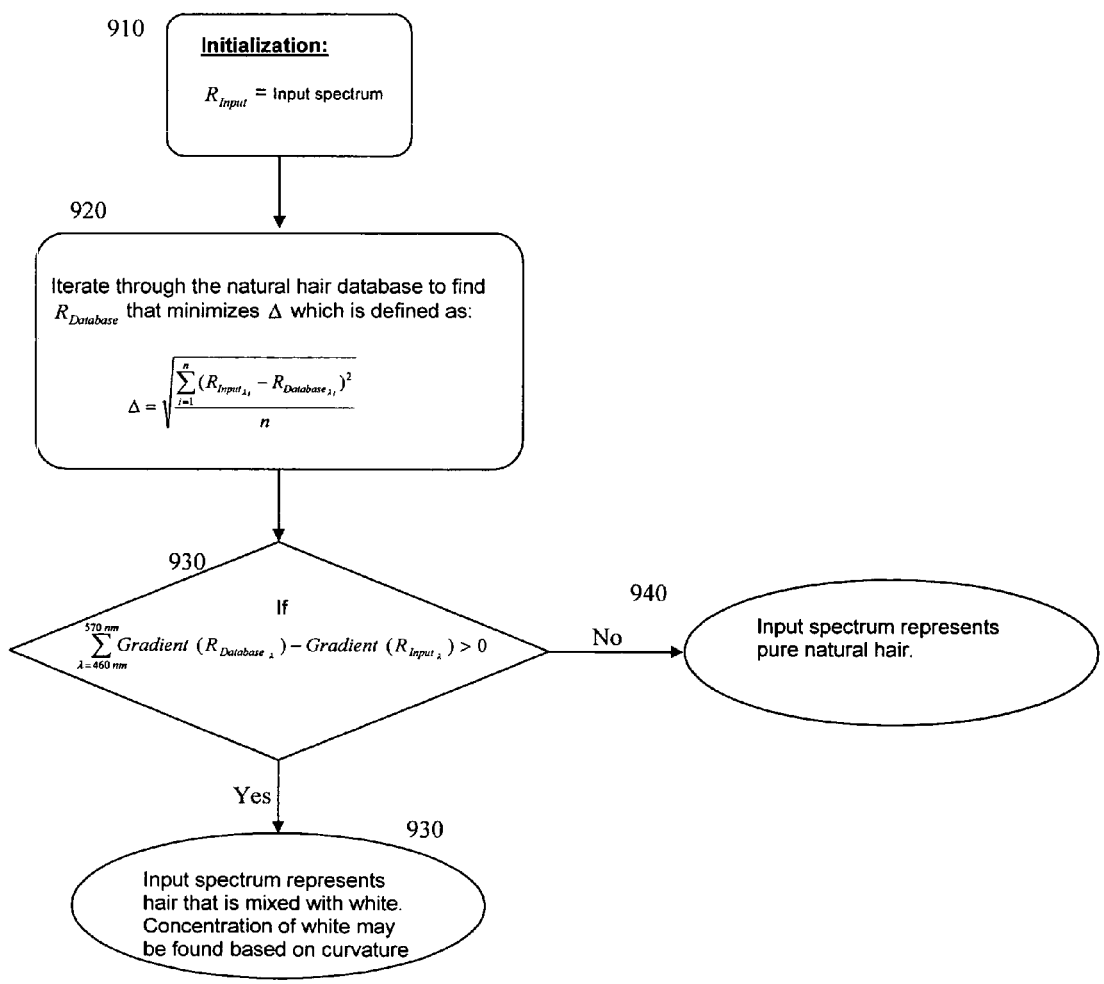

Reference is now made to FIG. 9 which is a detailed flowchart illustrating a sixth method for analyzing a sample hair mixture of two hair colors and an overall spectrum representative of the two colors, according to a preferred embodiment of the present invention.

A detailed example of the above described fifth method that may be implemented by an apparatus 3000 according to a preferred embodiment of the present invention includes the following steps:

First data relating to the best fitting spectrum is initiated 910.

Next, an iteration is made through the colored hair database, so as to find the spectrum best matching the overall spectrum of the hair mixture, according to the minimum RMS value criterion 920.

Then, a decision is made, according to the sum of gradient differences 920 between the hair mixture sample and the colored hair spectrum from the colored hair spectra database:

If the sum of gradient differences is greater then zero, the overall spectrum of the sample represents a hair which is mixed with white and an estimation is made with regard to the concentration of white hair in the sample hair mixture according to the curvature comparison made using the sum of gradient differences 930.

If the sum of gradient is zero, the overall spectrum represents a pure colored hair 940, free of white hair.

According to a preferred embodiment of the present invention, each of the methods, described hereinabove using FIG. 4-9, includes an additional step where a prediction is made with regard to the final color that results when the sampled hair mixture is dyed using a given hair dye.

After analyzing the mixture using one of the above mentioned methods, in order to find the reflectance spectrums of the colored component and the white component in the mixture, the prediction of the final color may be done for each of the spectrums separately using regular spectral prediction methods.

Once the final spectrums for each component are obtained, the prediction of the dyed mixture spectrum may be carried out using equation 1.1 with the found coefficients and the predicted components spectrums. The final spectrum of the hair mixture, upon applying a relevant color thereto, is therefore:

$$\text{predicted} R_{Mixture_\lambda} = (\text{predicted} R_{Natural_\lambda})^{foundCoeffNatural} \cdot (\text{predicted} R_{White_\lambda})^{foundCoeffWhite}$$

Thus a method, based on reflectance spectrum measurement according to a preferred embodiment of the present invention, may provide an accurate model for predicting a result of a final color of a given hair sample as a result of coloring with a single hair color, a mixture of hair colors, bleaching with an oxidative agent, etc.

A method according to a preferred embodiment of the present invention, may also overcome difficulties faced by known in the art methods when dealing with previously dyed hair.

Previous dyeing affects the hair reflectivity. However, it is found that most artificial colors mainly affect the red side of the hair spectrum which is the most reflective one. One solution may be to avoid the red side of the hair spectrum, say by using data in the 380 to 625 nanometers wavelength range only.

Other aspects of dealing with dyed hair are described in greater detail in U.S. patent application Ser. No. 11/066,205, filed on Mar. 28, 2005 entitled "Hair Coloring System", to Grossinger at at, which is hereby incorporated by reference.

It is expected that during the life of this patent many relevant devices and systems will be developed and the scope of the terms herein, particularly of the terms "spectrometer", "spectrum", "hair color" and "database", is intended to include all such new technologies a priori.

Additional objects, advantages, and novel features of the present invention will become apparent to one ordinary skilled in the art upon examination of the following examples, which are not intended to be limiting. Additionally, each of the various embodiments and aspects of the present invention as delineated hereinabove and as claimed in the claims section below finds experimental support in the following examples.

Reference is now made to FIG. 10 which is a line graph illustrating spectrums of exemplary hair samples. In the graph, each line represents a spectrum of white, colored, or mixed hair sample. Each spectrum line depicts the reflectance percentage as a function of wavelength, for a given white, colored, or mixed hair sample, as denoted using the provided legend 1010.

Reference is now made to FIG. 11 which is a line graph illustrating a hair sample mixture spectrum vs. a closely fitted colored spectrum.

In the graph, a line graph representative of a sample mixture spectrum is compared with a closely fitted colored hair color spectrum, selected from database of colored hair spectrums, utilizing methods based on RMS value minimization, as described in greater detail hereinabove.

Reference is now made to FIG. 12 which is a line graph illustrating resultant correlation between extracted concentrations and real concentrations of hair color in different mixtures.

In the provided example, a linear regression based correlation is found between coefficients found in different sample hair mixtures using the above discussed methods and real concentrations of white hair and colored hair in the sample hair mixtures.

As illustrated by the visual linear regression line 1210, and the correlation coefficient ($R^2=0.9889$) there is found strong correlation between the concentrations found using the above discussed methods and the real hair color concentrations in the provided hair mixture samples.

Reference is now made to FIG. 13 which is a line graph, illustrating a comparison between an extracted colored hair spectrum and the real spectrum.

As illustrated by the two graph lines, there is found strong correlation between a colored spectrum selected for a sample hair mixture, using the above described methods and the real spectrum of a sample.

Reference is now made to FIG. 14 which is a line graph illustrating curvature differences between a colored spectrum and a sample hair mixture spectrum.

In this example, there is provided a derivation graph indicating the curvature of a colored hair spectrum. The colored hair spectrum is fitted to an obtained overall spectrum of a sample hair mixture, using the above described methods. The example further provides a second derivation graph indicating the curvature of the obtained overall spectrum of a sample hair mixture.

Using the above discussed methods, the curvature difference between the two spectrums serves to find the existence and concentration of white hair in the sample hair mixture, as discussed in detail hereinabove.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. Apparatus for analyzing a sample hair mixture having a mixture of two hair colors and an overall reflectance spectrum representative of said two colors, comprising:
   a first color selector, configured to select a first reflectance spectrum representative of a first color in the hair mixture from a first group of at least one reflectance spectrum; and
   an iterative reflectance spectrum combiner, associated with said first color selector and configured to iteratively combine with said first reflectance spectrum successive candidates for a second reflectance spectrum representative of a second color in the hair mixture from a second group of reflectance spectra to form successive candidate combination spectra, and
   a spectrum selector to select from said successive candidate combination spectra an optimal one of said combination spectra which is a closest match to said overall reflectance spectrum, thereby to identify said two colors making up said mixture.

2. The apparatus of claim 1, further comprising a spectrometer, associated with said first color selector and operable for obtaining the overall spectrum.

3. The apparatus of claim 1, wherein said second group of spectra consists of at least one colored hair color spectrum.

4. The apparatus of claim 1, wherein at least one of said colored hair spectrums represents a non-natural hair color.

5. The apparatus of claim 1, wherein said first group of spectrums consists of at least one white hair color spectrum.

6. The apparatus of claim 1, wherein said selector is further configured to carry out said matching according to a measurement of difference between respective combination spectra and the overall spectrum.

7. The apparatus of claim 1, wherein said selector is further configured to carry out said matching according to a measurement being carried out for a group of more than ten points on respective combination spectra and the overall spectrum.

8. The apparatus of claim 1, wherein said selector is further configured to carry out said matching according to a root mean square (RMS) difference measurement between respective combination spectra and the overall spectrum.

9. The apparatus of claim 1, further comprising a final color predictor, associated with said iterative spectrum combiner and operable for predicting a spectrum of a final hair mixture, resultant upon applying a dyeing color to the sample hair mixture.

10. The apparatus of claim 1, wherein said iterative spectrum combiner is further configured to calculate concentration of said first color in said combination, for best matching said combination with the overall spectrum.

11. The apparatus of claim 1, wherein said iterative spectrum combiner is further configured to determine concentration of said first color in said combination according to a comparison of curvature of said second spectrum with curvature of the overall spectrum.

12. The apparatus of claim 1, wherein said spectrum selector is further configured to find the closest match to said overall spectrum among a group comprised of said optimal combination and previously found optimal combinations relating to the overall spectrum.

13. Apparatus for analyzing a sample hair mixture having a mixture of two hair colors and an overall spectrum representative of said two colors, comprising:
   an iterative spectrum combiner, configured to iteratively combine a first spectrum representative of a first color in the hair mixture from a first group of spectrums and a second spectrum representative of a second color in the hair mixture from a second group of spectrums into an optimized spectrum including a respective concentration of each of said first spectrum and second spectrum, said iterative spectrum combiner being further configured to calculate said concentrations to optimize fitness of said optimized spectrum to the overall spectrum; and
   a fitness optimizer, associated with said spectrum selector and spectrum calculator, configured to find among said optimized spectrums an optimized spectrum best fitting the overall spectrum.

14. The apparatus of claim 13, further comprising a spectrometer, associated with said iterative spectrum combiner and operable for obtaining said overall spectrum.

15. The apparatus of claim 13, wherein one of said groups of spectrums consists of at least one colored hair spectrum.

16. The apparatus of claim 15, wherein at least one of said colored hair spectrums represents a non-natural hair color.

17. The apparatus of claim 13, wherein one of said groups of spectrums consists of at least one white hair color spectrum.

18. The apparatus of claim 13, wherein said iterative spectrum combiner is further configured to determine said fitness according to a measurement of difference between each of said possible spectrums and the overall spectrum.

19. The apparatus of claim 13, wherein said iterative spectrum combiner is further configured to determine said fitness according to a measurement being carried out for a group of between ten and seventy five points on each of said possible spectrums and said overall spectrum.

20. The apparatus of claim 13, wherein said spectrum selector is further configured to determine said fitness according to a root mean square (RMS) difference measurement between each of said possible spectrums and the overall spectrum.

21. The apparatus of claim 13, further comprising a final color predictor, for predicting a spectrum of a final hair mixture, resultant upon applying a dyeing color to the sample hair mixture.

22. Apparatus for analyzing a sample hair mixture having a mixture of two hair colors and an overall reflectance spectrum representative of said two colors, comprising:
   a reflectance spectrum selector, configured to select a spectrum of colored hair such that said spectrum best fits the overall spectrum among a plurality of colored hair spectrums; and
   a curvature comparator, associated with said reflectance spectrum selector and configured to compare curvature of said selected spectrum with curvature of the overall spectrum and to determine concentration of white hair in the hair mixture according to said curvature comparison.

23. The apparatus of claim 22, further comprising a spectrometer, for obtaining the overall spectrum.

24. The apparatus of claim 22, wherein said curvature comparator is further configured to carry out said comparison of curvatures in a 460-570 nm wavelength range.

25. The apparatus of claim 22, wherein said spectrum selector is further configured to determine said fitness according to a measurement of difference between each of said colored hair spectrums and the overall spectrum.

26. The apparatus of claim 22, wherein said spectrum selector is further configured to determine said fitness according to a measurement being carried out for a group of between ten and seventy five points on each of said colored hair spectrums said overall spectrum.

27. The apparatus of claim 22, wherein said spectrum selector is further configured to determine said fitness according to a root mean square (RMS) difference calculation between each of said colored hair spectrums and the overall spectrum.

28. The apparatus of claim 22, further comprising a final color predictor, for predicting a spectrum of a final hair mixture, resultant upon applying a dyeing color to the sample hair mixture.

29. The apparatus of claim 22, wherein at least one of said colored hair spectrums represents a non-natural hair color.

30. Method for analyzing a sample hair mixture having a mixture of two hair colors and an overall reflectance spectrum representative of said two colors, comprising:
   a) selecting a first reflectance spectrum representative of a first color in the hair mixture from a first group of spectrums; and
   iteratively for different colors:
   b) selecting a second reflectance spectrum representative of a second color in the hair mixture from a second group of spectrums; and
   c) calculating an optimized reflectance spectrum based on said first spectrum, said second spectrum, and a respective concentration of each of said first spectrum and second spectrum, said concentrations calculated to optimized fitness of said optimized reflectance spectrum to the overall spectrum;
   until finding an optimized spectrum best fitting said overall reflectance spectrum.

31. The method of claim 30, further comprising an initial step of obtaining said overall spectrum.

32. The method of claim 30, wherein one of said groups of spectrums consists of at least one colored hair spectrum.

33. The method of claim 32, wherein at least one of said colored hair spectrums represents a non-natural hair color.

34. The method of claim 30, wherein one of said groups of spectrums consists of at least one white hair color spectrum.

35. The method of claim 30, wherein said fitness is determined according to a measurement of difference between said optimized spectrum and the overall spectrum.

36. The method of claim 30, wherein said iterative spectrum combiner is further configured to determine said matching according to a measurement being carried out for a group of between ten and seventy five points on each of said combination and the overall spectrum.

37. The method of claim 30, wherein said fitness is determined according to a root mean square (RMS) difference calculation between said optimized spectrum and the overall spectrum.

38. The method of claim 30, further comprising predicting a final color spectrum, resultant upon applying a dyeing color to the sample hair mixture.

39. Method for analyzing a sample hair mixture having a mixture of two hair colors and an overall reflectance spectrum representative of said two colors, comprising:

selecting a reflectance spectrum representative of colored hair such that said spectrum best fits the overall spectrum among a plurality of colored hair spectrums;

comparing curvature of the overall reflectance spectrum with curvature of said selected spectrum; and finding a concentration of white hair color in the hair mixture according to said curvature comparison.

40. The method of claim 39, further comprising obtaining the overall spectrum before said selecting a spectrum.

41. The method of claim 39, wherein said comparison of curvatures is carried out in a 460-570 nm wavelength range.

42. The method of claim 39, wherein said fitting is determined according to a measurement of difference between said selected spectrum and the overall spectrum.

43. The method of claim 39, wherein said fitting is determined according to a root mean square (RMS) difference calculation between said selected spectrum and the overall spectrum.

44. The method of claim 39, further comprising predicting a final color spectrum, resultant upon applying a dyeing color to the sample hair mixture.

45. The method of claim 39, wherein at least one of said colored hair spectrums represents a non-natural hair color.

46. A method of dying hair having a mixture of two hair colors and an overall reflectance spectrum representative of said two colors, comprising:

a) selecting a first reflectance spectrum representative of a first color in the hair mixture from a first group of spectrums; and iteratively for different colors:

b) selecting a second reflectance spectrum representative of a second color in the hair mixture from a second group of spectrums; and c) calculating an optimized reflectance spectrum based on said first spectrum, said second spectrum, and a respective concentration of each of said first spectrum and second spectrum, said concentrations calculated to optimized fitness of said optimized spectrum to the overall spectrum;

until finding an optimized spectrum best fitting said overall spectrum, and prescribing a hair dyeing treatment according to said found optimized spectrum.

47. A method of selecting dye ingredients for dyeing hair having a mixture of two hair colors and an overall reflectance spectrum representative of said two colors, comprising:

a) selecting a first reflectance spectrum representative of a first color in the hair mixture from a first group of spectrums; and iteratively for different colors:

b) selecting a second reflectance spectrum representative of a second color in the hair mixture from a second group of spectrums; and c) calculating an optimized reflectance spectrum based on said first spectrum, said second spectrum, and a respective concentration of each of said first spectrum and second spectrum, said concentrations calculated to optimized fitness of said optimized spectrum to the overall spectrum;

until finding an optimized reflectance spectrum best fitting said overall spectrum, and prescribing ingredients for a hair dyeing treatment according to said found optimized reflectance spectrum.

* * * * *